United States Patent [19]

De Labbey et al.

[11] Patent Number: 5,648,069
[45] Date of Patent: Jul. 15, 1997

[54] 4-[(2-OXO-3-BORNYLIDENE) METHYL] PHENYLTRIMETHYLAMMONIUM METHYL SULFATE IN A PERMANENT HAIR SHAPING COMPOSITION FOR PROTECTION AGAINST THE RAVAGES OF THE WEATHER AND IN PARTICULAR AGAINST LIGHT

[75] Inventors: Arnaud De Labbey, Aulnay-sous-Bois; Ly Lan N'guyen, L'Hay-les-Roses, both of France

[73] Assignee: L'Oreal, Paris, France

[21] Appl. No.: 256,075

[22] PCT Filed: Dec. 22, 1992

[86] PCT No.: PCT/FR92/01223

§ 371 Date: Aug. 19, 1994

§ 102(e) Date: Aug. 19, 1994

[87] PCT Pub. No.: WO93/12763

PCT Pub. Date: Jul. 8, 1993

[30] Foreign Application Priority Data

Dec. 23, 1991 [FR] France ................................. 91 16019

[51] Int. Cl.⁶ .............................. A61K 7/09; A61K 7/92
[52] U.S. Cl. ................................ 424/70.2; 424/70.9
[58] Field of Search ............... 424/70.9, 70.2–70.51, 424/401, 59

[56] References Cited

U.S. PATENT DOCUMENTS

| | | | |
|---|---|---|---|
| 3,988,110 | 10/1976 | Zviak | 424/70.9 |
| 4,061,730 | 12/1977 | Kalopissis et al. | 424/59 |
| 4,323,599 | 4/1982 | Bouillon | 424/70.9 |
| 4,656,029 | 4/1987 | Grollier | 424/70.9 |
| 5,004,594 | 4/1991 | Richard | 424/70.9 |
| 5,102,660 | 4/1992 | Forestier | 424/70.9 |

FOREIGN PATENT DOCUMENTS

| | | |
|---|---|---|
| 0329032 | 2/1988 | European Pat. Off. . |
| 0440547 | 8/1991 | European Pat. Off. . |
| 2199971 | 4/1974 | France . |

OTHER PUBLICATIONS

Zviak *The Science of Hair Care*, 1986 pp.115–116 117.

*Primary Examiner*—Sallie M. Gardner
*Attorney, Agent, or Firm*—Jacobson, Price, Holman & Stern, PLLC

[57] ABSTRACT

Use of 4-[2-oxo-3-bornylidene)methyl]-phenyltrimethylammonium methyl sulphate to preserve the hair's mechanical properties, and especially its elasticity, from the ravages caused by the successive action of permanent hair shaping and light. The compound is for use in a quantity of between 0.05 and 15% by weight, in an aqueous reducing or setting composition or a composition employed in between these two steps, to achieve permanent hair shaping.

5 Claims, No Drawings

4-[(2-OXO-3-BORNYLIDENE) METHYL] PHENYLTRIMETHYLAMMONIUM METHYL SULFATE IN A PERMANENT HAIR SHAPING COMPOSITION FOR PROTECTION AGAINST THE RAVAGES OF THE WEATHER AND IN PARTICULAR AGAINST LIGHT

Use of 4-[(2-oxo-3-bornylidene)methyl] phenyltrimethylammonium methyl sulfate in a permanent hair shaping composition for protection against the ravages of the weather and in particular against light.

The subject of the present invention is the use of 4-[(2-oxo-3-bornylidene)methyl]phenyltrimethylammonium methyl sulfate in a permanent hair shaping composition as an agent for protecting the keratin of hair against the ravages of the weather, and in particular against light, and a process for protecting the mechanical properties of hair subjected to the successive action of a permanent hair shaping treatment and the ravages of the weather, in particular light, using this compound.

It has long been known that light attacks hair keratin. Numerous publications disclose that natural light destroys certain amino acids in hair and that by damaging the hair fiber it degrades its mechanical properties; degradation of the mechanical properties is principally understood to mean the decrease of the 15% extension stage.

The 15% extension stage is the weight which must be applied to a wet hair of a given length in order to lengthen it by 15%. The heavier the weight, the stronger and more elastic is the hair.

In order to combat the attack of hair by light, it has already been proposed to use substances which are capable of filtering light radiation.

As agents for protecting the mechanical properties of hair and essentially of the wet 15% extension stage, the Applicant has previously proposed, in Patent Application EP 329,032 and French Patent Application 2,627,085, screening agents such as 4-(2-oxo-3-bornylidenemethyl) benzenesulfonic acid or salts thereof and 2-hydroxy-4-methoxybenzophenone-5-sulfonic acid or salts thereof.

These compounds have in particular been recommended for application before or after shampooing, dyeing, bleaching, permanent waving or straightening of the hair.

It is moreover known to use substantive screening substances such as particular quaternary ammonium salts of carboxylic acids described in U.S. Pat. No. 4,680,144, with the aim of preventing the fading of the artificial color of the hair by light. The said substances have been recommended in the form of shampoos or sprays to be applied after dyeing.

Patent FR 2,509,989 cites water-soluble sunscreen agents which may be used in the aqueous phase of a cosmetic composition for protecting the skin and hair against UV radiation, this composition comprising a distinct oily phase. No indication as to the type of hair protected or to the mechanical properties of the hair is made therein.

In the prior art, no screening substance has, therefore, yet been recommended for use in a permanent hair shaping composition with the aim of protecting the mechanical properties of permanent waved hair, and in particular its elasticity, from light.

Now, it is well known that the maximum degradation of the mechanical properties, and in particular of the elasticity, is observed in the case of hair subjected to a permanent shaping operation and then subsequently attacked by light. This is related to increased embrittlement of the hair by the cumulative action of the reducing agent and of the fixative.

In this specific case, no screening substance has yet proved sufficiently effective at protecting hair subjected to a permanent shaping operation and to the successive action of light.

The Applicant has now surprisingly discovered that 4-[(2-oxo-3-bornylidene)methyl] phenyltrimethylammonium methyl sulfate was able effectively to protect the mechanical properties of hair subjected to a permanent shaping operation, in particular its elasticity, against degradation by the ravages of the weather, and in particular light, when the abovementioned active compound is introduced in aqueous solution either into the reducing phase or into the oxidizing, so-called fixing, phase or by intrapermanent application, that is to say between the two steps of reduction and fixing.

This property was able to be demonstrated by exposure under natural light (sunny environment) and under artificial light (xenon emitter of an accelerated aging apparatus of the SUNTEST HANAU type).

4-[(2-Oxo-3-bornylidene)methyl] phenyltrimethylammonium methyl sulfate is described in French Patent 2,199,971 as a UV screening agent which may be applied to hair or incorporated in cosmetic compositions containing photosensitive constituents.

The aim of the present invention is thus the use of 4-[(2-oxo-3-bornylidene)methyl] phenyltrimethylammonium methyl sulfate in a permanent hair shaping composition in the form of an aqueous solution, as an agent for protecting the mechanical properties of hair and essentially its elasticity, measured by the wet 15% extension stage, against degradation brought about by the successive action of a permanent hair shaping and the ravages of the weather, in particular light.

According to the invention and advantageously, it has been observed that this protection proved to be long-lasting even after shampooing, and that it additionally allowed permanent waved or straightened hair to be dyed with shades having a better resistance to light.

In the invention, 4-[(2-oxo-3-bornylidene)methyl] phenyltrimethylammoniummethyl sulfate is used in amounts between 0.05 and 15%, and preferably between 1 and 10% by weight, relative to the total weight of the reduction composition or of the fixing composition or alternatively of the intrapermanent composition.

When the screening agent is used in the reducing composition, it is preferred to use the screening agent and the reducing agent in an extemporaneous mixture which is prepared at the time of use.

The reduction and fixing compositions may contain all the ingredients known in the prior art for performing a permanent waving or straightening operation on the hair, for example as are described in Harry's Cosmeticology, 7th edition-1982, p. 569–577.

The intrapermanent compositions are essentially aqueous and optionally thickened compositions. They may contain, as may the reduction and fixing compositions, adjuvants which make it possible to improve the cosmetic state of the hair fibers, among which there may be mentioned, by way of examples, natural plant or synthetic proteins which may be quaternized, amino acids or polymers; they may also contain agents for strengthening the hair fiber, among which there may for example be mentioned inorganic or organic water-soluble salts of divalent metals, such as magnesium chloride, sulfate, aspartate or acetate.

The present invention also concerns a process for protecting the mechanical properties, and essentially the elasticity measured by the wet 15% extension stage, of hair subjected to the successive action of a permanent shaping treatment and the ravages of the weather, in particular light, consisting in applying to the hair an aqueous reducing or fixing composition or a so-called "intrapermanent" composition used between the two steps of reduction and fixing of the permanent shaping treatment, containing an effective amount of 4-[(2-oxo-3-bornylidene)methyl]phenyltrimethylammonium methyl sulfate.

The examples which follow illustrate the invention without, however, limiting it.

EXAMPLE 1

A reducing composition for the permanent waving of hair and having the following composition is prepared:

| | |
|---|---|
| Thioglycolic acid | 6.7 g |
| Ammonium carbonate | 5.6 g |
| 4-[(2-Oxo-3-bornylidene)methyl]phenyl-trimethylammonium methyl sulfate | 5.0 g |
| Oleocetyldimethylammonium chloride | 1.5 g |
| Aqueous ammonia qs pH: 8.0 | |
| Perfume, stabilizing agent qs | |
| Demineralized water qs | 100 g |

This composition is prepared extemporaneously by adding 5 g of 4-[(2-oxo-3-bornylidene)methyl]phenyltrimethylammonium methyl sulfate to the remainder of the composition.

This composition is applied to wet hair which has been wound previously on hair rollers. It is left to act for 15 minutes and is then rinsed copiously with water.

The following oxidizing composition is then applied:

| | |
|---|---|
| Aqueous 200 volumes hydrogen peroxide solution | 4.8 g |
| Stabilizers: 8-hydroxyquinoline sulfate and phenacatin | 0.06 g |
| Oleyl alcohol containing 20 moles of ethylene oxide | 1.5 g |
| Citric acid qs pH: 3 | |
| Demineralized water qs | 100 g |

The oxidizing composition is left to act for 10 minutes. The hair is rinsed with water and then the rollers are removed and it is dried.

The hair is then exposed for 120 hours to the SUNTEST using a "SUNTEST HANAU" apparatus. This apparatus consists of a xenon emitter and a system of filters which produce radiation which corresponds, in a very large measure, to solar radiation. The radiation energy is approximately 585 W/m$^2$ in the wavelength range between 300 and 830 nm (global irradiants).

The permanent wave thus produced makes it possible, by virtue of the active compound introduced into its reduction phase, to improve the average wet 15% extension stage very significantly relative to identically permanent-waved hair of the same nature but without 4-[(2-oxo-3-bornylidene)methyl]phenyltrimethylammonium methyl sulfate in the reduction phase.

EXAMPLE 2

The following reducing composition is prepared:

| | |
|---|---|
| Thioglycolic acid | 9.3 g |
| Monoethanolamine | 3.1 g |
| Ammonium carbonate | 3.0 g |

-continued

| | |
|---|---|
| Mixture of cocoamidopropylbetaine and glyceryl laurate sold under the name "Tégobétaine HS" (GOLDSCHMIDT), in solution at a concentration of 30% AM | 0.7 g AM |
| Aqueous ammonia qs pH: 8.3 | |
| Perfume, stabilizing agent qs | |
| Demineralized water qs | 100 g |

This composition is applied to wet hair which has been wound beforehand on hair rollers; it is left to act for 15 minutes and is then rinsed copiously.

The following intrapermanent lotion is then applied:

| | |
|---|---|
| Magnesium chloride | 1.1 g |
| L-aspartic acid | 0.4 g |
| L-isoleucine | 0.4 g |
| Glycine | 0.4 g |
| D,L-serine | 0.4 g |
| Quaternized protein resulting from the condensation of cocoamidopropyldimethylamine with a hydrolyzed animal protein, named in the supplement to the 4th edition (1991) of the CTFA dictionary as: Quaternium-76 Hydrolyzed Collagen, sold under the trade name "LEXEIN QX 3000" by the company INOLEX | 2.3 g |
| Sorbic acid | 0.3 g |
| 4-[(2-Oxo-3-bornylidene)methyl]phenyltrimethyl-ammonium methyl sulfate | 3.0 g |
| Demineralized water qs | 100 g |

It is left in contact with the hair for 5 minutes and, without rinsing, the following fixing composition is applied:

| | |
|---|---|
| Aqueous 200 volumes hydrogen peroxide solution | 4.8 g |
| Stabilizing agents: 8-hydroxyquinoline sulfate and phenacetin | 0.06 g |
| Distearyldimethylammonium chloride | 0.5 g |
| Citric acid qs pH: 3 | |
| Demineralized water qs | 100 g |

It is left to stand for 10 minutes. The hair is rinsed with water, the rollers are removed and it is dried.

The hair is subsequently exposed for 120 hours to the SUNTEST, as described in Example 1.

Compared with identically permanent-waved hair of the same nature but without the active compound: 4-[(2-oxo-3-bornylidene)methyl]phenyltrimethylammonium methyl sulfate in the intrapermanent composition, an appreciable improvement in the average value of the wet 15% extension stage is observed.

EXAMPLE 3

The following reducing composition is prepared:

| | |
|---|---|
| Thioglycolic acid | 7.5 g |
| Ammonium carbonate | 4.0 g |
| Oleocetyldimethylammonium chloride | 1.2 g |
| Aqueous ammonia qs pH: 8.1 | |
| Perfume, stabilizing agent qs | |
| Demineralized water qs | 100 g |

This composition is applied to wet hair which has been wound beforehand on hair rollers. It is left to act for 15 minutes and is then rinsed copiously with water.

The following fixing composition is then applied for 10 minutes:

| | |
|---|---|
| Aqueous 200 volumes hydrogen peroxide solution | 4.8 g |
| Stabilizing agents: 8-hydroxyquinoline sulfate and phenacetin | 0.06 g |
| Lauryldimethylamine oxide | 0.7 g |
| 4-[(2-Oxo-3-bornylidene)methyl]phenyltrimethylammonium methyl sulfate | 3.0 g |
| Demineralized water qs | 100 g |

It is left to act for 10 minutes and the hair is rinsed and dried.

The hair is subsequently exposed for 120 hours to the SUNTEST, as described in Example 1.

Compared with identically permanent-waved hair of the same nature but without the active compound: 4-[(2-oxo-3-bornylidene)methyl]phenyltrimethylammonium methyl sulfate in the fixing composition, an appreciable improvement in the value of the wet 15% extension stage and a cosmetic improvement in the state of the permanent-waved hair are observed.

EXAMPLE 4

Example 1 is repeated, proceeding, after the permanent waving and before the exposure to the SUNTEST, to a dyeing of the hair thus permanent-waved.

Compared with hair of the same nature permanent-waved in the absence of the active compound in the reduction phase, and then dyed before being subjected to the same exposure, a greater color fastness is observed.

EXAMPLE 5

Example 2 is repeated, retaining the reducing composition and the fixing composition, and using an intrapermanent lotion having another composition and comprising:

| | |
|---|---|
| Magnesium aspartate | 2.0 g |
| L-aspartic acid | 0.5 g |
| L-isoleucine | 0.5 g |
| Glycine | 0.5 g |
| D,L-serine | 0.5 g |
| Quaternized hydrolyzate of wool keratin (MW = 1000), in aqueous solution at a concentration of 25% AM (PROMOIS WK-HQ sold by SEIWA KASEI) | 1.5 g AM |
| Sorbic acid | 0.3 g |
| 4-[(2-Oxo-3-bornylidene)methyl]phenyltrimethylammonium methyl sulfate | 4.0 g |
| Demineralized water qs | 100 g |

After exposure for 120 hours to the SUNTEST, a notable improvement is observed in the average value of the wet 15% extension stage relative to identically permanent-waved hair of the same nature but without the active compound.

We claim:

1. In a permanent waving composition consisting essentially of a reduction composition in the form of an aqueous solution having a reducing agent or a fixing composition in the form of an aqueous solution having an oxidation agent, the improvement comprising 1 to 10% by weight, relative to the total weight of the permanent waving composition, of 4-[(2-oxo-3-bornylidene)methyl]phenyltrimethylammoniummethyl sulfate dissolved in the permanent waving composition for protecting the elasticity of hair measured by a wet 15% extension stage from degradation brought about by the successive action of a permanent waving and the ravages of weathering.

2. Composition according to claim 1 wherein the composition contains plant or synthetic proteins which may be quaternized, amino acids, polymers or inorganic or organic water-soluble salts of divalent metals.

3. A method of protecting elasticity properties of hair measured by a wet 15% extension stage during a permanent waving treatment against degradation brought about by the successive action of permanent waving and the ravages of weathering, comprising applying to the hair a 1–10% by weight aqueous solution of 4-[(2-oxo-3-bornylidene)methyl]phenyltrimethylammonium methyl sulfate together with a reducing agent in the reducing phase of said permanent waving treatment or together with an oxidation agent in the oxidizing phase of said permanent waving treatment or after application of a reducing agent to the hair and before the application of an oxidation agent to the hair to complete the waving treatment wherein in the last case said aqueous solution is not rinsed prior to application of the oxidation agent.

4. Method according to claim 3, wherein the 4-[(2-oxo-3-bornylidene)methyl]phenyltrimethylammonium methyl sulfate and the reducing agent are mixed at the time of use.

5. Method according to claim 3, wherein plant or synthetic proteins which may be quaternized, amino acids, polymers or inorganic or organic water-soluble salts of divalent metals are introduced into the aqueous solution.

* * * * *